(12) United States Patent
Langan et al.

(10) Patent No.: US 7,782,998 B2
(45) Date of Patent: Aug. 24, 2010

(54) METHOD AND APPARATUS FOR CORRECTING MOTION IN IMAGE RECONSTRUCTION

(75) Inventors: David Langan, Clifton Park, NY (US); Peter Edic, Albany, NY (US); Abdalmajeid Alyassin, Niskayuna, NY (US); Bernhard Claus, Niskayuna, NY (US); Joseph Manak, Albany, NY (US); James V. Miller, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 743 days.

(21) Appl. No.: 11/018,030

(22) Filed: Dec. 21, 2004

(65) Prior Publication Data

US 2006/0133564 A1 Jun. 22, 2006

(51) Int. Cl.
*A61B 6/00* (2006.01)
(52) U.S. Cl. ........................................................ 378/8
(58) Field of Classification Search .................. 378/4, 378/5–11, 15–20, 91, 95, 98.8
See application file for complete search history.

(56) References Cited

U.S. PATENT DOCUMENTS

| 4,190,772 | A | * | 2/1980 | Dinwiddie et al. ............. 378/15 |
| 4,334,154 | A | * | 6/1982 | Sandland ......................... 378/4 |
| 4,994,965 | A | * | 2/1991 | Crawford et al. ............... 378/95 |
| 5,195,114 | A | * | 3/1993 | Sairenji et al. ................. 378/40 |
| 5,491,734 | A | | 2/1996 | Boyd et al. .................... 378/10 |
| 5,671,263 | A | * | 9/1997 | Ching-Ming ................... 378/8 |
| 5,719,914 | A | | 2/1998 | Rand et al. ..................... 378/4 |
| 5,852,646 | A | * | 12/1998 | Klotz et al. ..................... 378/8 |
| 6,130,929 | A | | 10/2000 | Saha ............................... 378/4 |
| 6,154,516 | A | * | 11/2000 | Heuscher et al. .............. 378/15 |
| 6,208,711 | B1 | | 3/2001 | Rand et al. .................... 378/138 |
| 6,233,478 | B1 | * | 5/2001 | Liu ............................... 600/428 |
| 6,324,254 | B1 | * | 11/2001 | Pflaum ........................ 378/95 |
| 6,370,217 | B1 | * | 4/2002 | Hu et al. ......................... 378/8 |
| 6,385,285 | B1 | * | 5/2002 | Vaillant et al. ................ 378/62 |
| 6,470,066 | B2 | * | 10/2002 | Takagi et al. .................... 378/8 |

(Continued)

FOREIGN PATENT DOCUMENTS

WO    WO 03/101300 A2 * 12/2003

OTHER PUBLICATIONS

Rasche et al., ECG-gated 3D-rotational coronary angiography (3DRCA), Computer Assisted Radiology and Surgery Cars 2002, 2002, pp. 827-831.*

(Continued)

*Primary Examiner*—Edward J Glick
*Assistant Examiner*—Alexander H Taningco
(74) *Attorney, Agent, or Firm*—Jason K. Klindtworth

(57) ABSTRACT

A plurality of projection images are acquired over an angular range during the slow rotation of a C-arm gantry having a source and detector. Phase-specific reconstructions are generated from the plurality of projections, wherein each phase-specific reconstruction is generated generally from projections acquired at or near the respective phase. In one embodiment, a plurality of motion estimates are generated based upon the phase-specific reconstructions. One or more motion-corrected reconstructions may be generated using the respective motion estimates and projections. The motion-corrected reconstructions may be associated to form motion-corrected volume renderings.

13 Claims, 2 Drawing Sheets

U.S. PATENT DOCUMENTS

| | | | |
|---|---|---|---|
| 6,510,337 B1* | 1/2003 | Heuscher et al. | 600/428 |
| 6,522,712 B1* | 2/2003 | Yavuz et al. | 378/4 |
| 6,529,575 B1* | 3/2003 | Hsieh | 378/4 |
| 6,535,570 B2* | 3/2003 | Stergiopoulos et al. | 378/8 |
| 6,628,742 B2* | 9/2003 | Pan et al. | 378/8 |
| 6,904,119 B2* | 6/2005 | Oikawa | 378/15 |
| 7,020,234 B2* | 3/2006 | Bruder et al. | 378/8 |
| 2002/0048343 A1* | 4/2002 | Launay et al. | 378/98.12 |
| 2002/0106052 A1* | 8/2002 | Menhardt | 378/4 |
| 2002/0126794 A1* | 9/2002 | Rasche et al. | 378/8 |
| 2002/0181645 A1* | 12/2002 | Bruder et al. | 378/8 |
| 2003/0016782 A1* | 1/2003 | Kaufman et al. | 378/50 |
| 2003/0161436 A1* | 8/2003 | Boyd et al. | 378/8 |
| 2004/0017881 A1* | 1/2004 | Cesmeli et al. | 378/4 |
| 2004/0125908 A1* | 7/2004 | Cesmeli et al. | 378/4 |
| 2004/0136490 A1* | 7/2004 | Edic et al. | 378/4 |
| 2005/0069081 A1* | 3/2005 | Kokubun et al. | 378/15 |
| 2005/0113680 A1* | 5/2005 | Ikeda et al. | 600/425 |
| 2005/0123094 A1* | 6/2005 | Suzuki | 378/98.12 |
| 2005/0201509 A1* | 9/2005 | Mostafavi et al. | 378/8 |
| 2006/0210019 A1* | 9/2006 | Rasche et al. | 378/62 |

OTHER PUBLICATIONS

Blondel et al., Reconstruction of Coronary Arteries from One Rotational X-ray Projection Sequence, INRIA, 2004, pp. 1-43.*

U.S. Appl. No. 10/625,719, filed Jul. 23, 2003, Douglas Perry Boyd et al.

U.S. Appl. No. 10/625,361, filed Jul. 23, 2003, Peter Michael Edic et al.

* cited by examiner

METHOD AND APPARATUS FOR CORRECTING MOTION IN IMAGE RECONSTRUCTION

BACKGROUND OF THE INVENTION

The present invention relates generally to the field of non-invasive imaging and more specifically to the field of medical imaging for dynamic, internal tissue, such as cardiac tissue. In particular, the present invention relates to the characterization of internal motion and to the reconstruction of images that account for the characterized motion.

Non-invasive medical imaging broadly encompasses techniques for generating images of the internal structures or regions of a person that are otherwise inaccessible for visual inspection. One of the best known uses of non-invasive imaging is in the medical arts where these techniques are used to generate images of organs and/or bones inside a patient which would otherwise not be visible. One class of medical non-invasive imaging techniques is based on the differential transmission of X-rays through a patient. For example, a simple X-ray imaging technique may involve generating X-rays using an X-ray tube or other X-ray source and directing the X-rays through an imaging volume in which the part of the patient to be imaged is located. As the X-rays pass through the patient, the X-rays are attenuated based on the composition of the tissue they pass through. The attenuated X-rays then impact a detector that converts the X-rays into signals that can be processed to generate an image of the part of the patient through which the X-rays passed based on the attenuation of the X-rays.

Three-dimensional information may be obtained by obtaining additional images at different viewing angles relative to the imaging volume. The angularly displaced images acquired in this manner may then be reconstructed to produce a three-dimensional representation of the imaging volume, including internal structures and organs, that may be displayed on a monitor, printed to a printer, or reproduced on film. A technologist may then review the three-dimensional representation, such as to detect clinically significant irregularities or abnormalities or to assess the three-dimensional landscape prior to an invasive or non-invasive surgical procedure.

Dynamic internal tissues, such as the heart, may present certain challenges for non-invasive imaging techniques, however. For example, in cardiac imaging, the motion of the heart results in inconsistencies in imaging data acquired at different phases of the cardiac cycle. These inconsistencies cause various motion-related image artifacts, such as blurring, streaking, or discontinuities, in the images and/or volumes generated with the imaging data. To reduce the occurrence of motion-related image artifacts, various techniques may be employed to improve the temporal resolution of the imaging system, thereby reducing the effects of the movement of the tissue. For example, temporal resolution may generally be improved by decreasing the time over which the imaging data is acquired. In this way, the amount of motion that occurs within the temporal window associated with the acquisition of the imaging data set is minimized. The temporal resolution may be further improved by choice of reconstruction algorithms and/or techniques. However, these various techniques, alone and in combination, are not currently capable of providing a temporal resolution of approximately 20 ms or less, which is desirable to "freeze" cardiac motion, thereby minimizing motion related artifacts in the reconstructed images. A technique for achieving a temporal resolution consistent with the mechanical and computational constraints present in an imaging system is therefore desirable.

BRIEF DESCRIPTION OF THE INVENTION

In accordance with an exemplary embodiment of the present technique, a method is provided for generating phase specific reconstructions. The method includes acquiring a plurality of projection images during a slow rotation over a limited angular range. A plurality of phase-specific reconstructions are generated. Each phase specific reconstruction is generated based on at least a subset of the plurality of projections acquired at or near the respective phase, such as of a cardiac cycle. A computer-readable media is also provided that affords functionality of the type defined by this method.

An image analysis system is provided. The image analysis system comprises a workstation configured to generate a plurality of phase-specific reconstructions. Each phase-specific reconstruction is generated based on at least a subset of projections acquired at or near the respective phase. The subset is part of a plurality of projections acquired over a limited angular range during a slow rotation.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
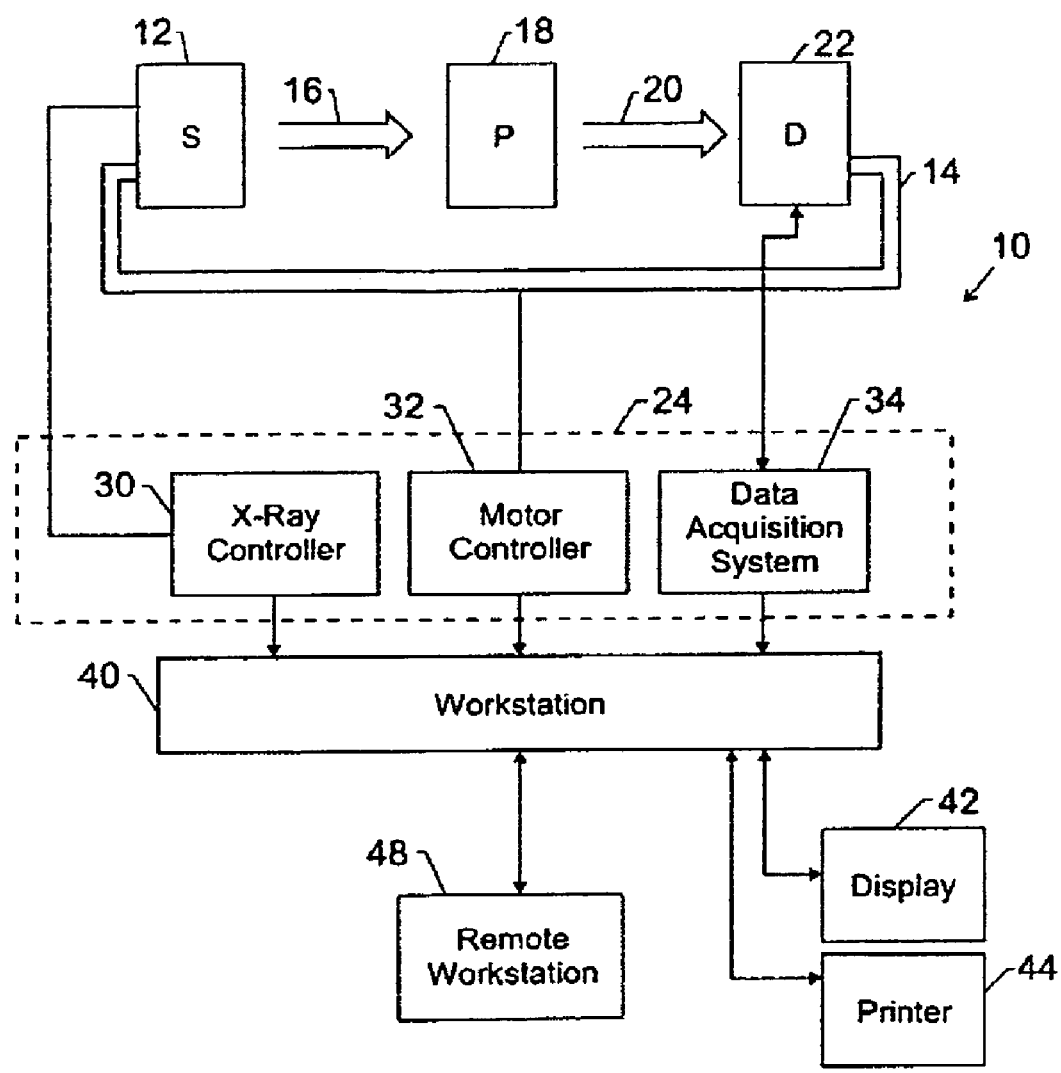
FIG. 1 is a diagrammatical view of an exemplary imaging system for use in accordance with the present technique.

FIG. 1 illustrates diagrammatically an imaging system 10 for acquiring and processing image data. In the illustrated embodiment, system 10 is an imaging system employing a C-arm type gantry designed to acquire X-ray projection data at various viewing angles about an imaging volume, to reconstruct the projection data into an image, and to process the image data for display and analysis in accordance with the present technique. For example, the imaging system 10 may be a fixed C-arm vascular imaging system, such as may be present in a dedicated imaging or examination room, or a mobile C-arm vascular imaging system, such as may be used in surgical procedures or moved within a medical facility as needed. The imaging system 10 may also be a tomosynthesis system or other imaging system configured to acquire image data over a limited angular range or a computed tomography (CT system configured to acquire image data over a complete angular range.

In the embodiment illustrated in FIG. 1, imaging system 10 includes a source of X-ray radiation 12 attached to one end of a C-arm 14. In one embodiment, the source of X-ray radiation source 12 is typically an X-ray tube. In other embodiments, the source 12 may be a solid state X-ray emitter or any other X-ray source suitable for generating and emitting X-rays having a suitable X-ray spectrum for the desired imaging procedure. The source 12 may include a collimation or beam-shaping component, such as lead or tungsten shutter, to shape the emitted stream of radiation 16 passing through the imaging volume toward the other end of the C-arm 14. For simplicity, the imaging system 10 of FIG. 1 is depicted as including a single C-arm 14 and associated source 12 and detector 22. However, as will be appreciated by those of ordinary skill in the art, additional C-arms 14 (and associated sources 12 and detectors 22) may be present in the imaging system 10. In embodiments employing multiple C-arm gantries, the motion of the C-arms may be coordinated or may be independent of one another. Such bi-planar and/or multi-planar C-arm imaging systems, may be used in accordance with the present technique in the manner set forth below in the context of an exemplary single C-arm imaging system.

Returning now to FIG. 1, an unattenuated portion of the radiation 20 that passes through the portion of the patient 18 to be imaged impacts a detector array, represented generally as reference numeral 22. Detector elements of the array produce electrical signals that represent the intensity of the incident X-ray beam. The signals generated by the detector array 22 may be subsequently processed to reconstruct an image of the features within the subject.

A variety of configurations of the detector 22 may be employed in conjunction with the techniques described herein. In one embodiment, the detector 22 is a high-resolution flat-panel detector array, comprising hundreds of rows of detector elements. In this embodiment, the detector array panel may be about 20 cm to 40 cm or greater on a side. Typically the detector 22 is sized such that the entire object or organ being imaged may be positioned within the field of view provided by the detector 22 while the C-arm 14 is rotated. For example, in an embodiment used for three-dimensional reconstruction, the detector 22 would typically be sized such that the entire volume (skin line to skin line) that contains the organ of interest is in the field of view provided by the detector 22. In general, the detector should encompass the entire object or organ being imaged in such an embodiment. If objects are present in only a subset of the projections acquired by the detector 22, the reconstruction algorithm used to process the projections must account for these data irregularities. Other configurations of detector 22 may also be suitable. For example, a curved detector array may be employed in some embodiments. Similarly, an image intensifer or alternative detection technology may be employed in other embodiments. In general, it is desirable to center the object or organ to be imaged, particularly a dynamic organ such as the heart, within the field of view defined by the detector array 22.

In some embodiments, the portion of the detector array from which signals are acquired, i.e., the portion of the panel that is "read out," may be varied. For example, in embodiments where the detector array 22 provides a field of view larger than the organ being imaged, only those rows of the detector that minimize the volume containing the organ may be read out, thus increasing the image acquisition speed. In this manner, image acquisition speed may be increased for those parts of the cardiac cycle in which the heart undergoes rapid motion. In such embodiments, the region of the detector 22 to be read out may be determined based upon estimates of the heart region within previously acquired images during the examination. In other embodiments, to further increase image acquisition speed during periods of rapid cardiac motion, the portion of the detector read out may be less than the entire volume containing the organ, but rather be limited to the organ itself. In such an embodiment, the effect of data truncation may be managed by holding the overall angular distribution of acquired projection images for non-moving regions of the volume containing the heart approximately constant.

In one embodiment, the detector 22 includes a reference region. In this embodiment, the path between the source 12 and the reference region is unobstructed. Because of this unobstructed path, the signal acquired at the reference region can be used to normalize the projection data acquired at each view angle position, accounting for minor fluctuations in tube current such that an apparent constant operating current of the X-ray tube is achieved during image data acquisition. In other embodiments, the detector 22 includes a distinct reference detector configured to acquire the normalization signal. This normalization process may be performed in addition to standard gain normalization processes implemented for typical computed tomography reconstruction.

In the depicted embodiment, the source 12 is controlled by an X-ray controller 30. Particularly, the X-ray controller 30 is configured to provide power and timing signals to the X-ray source 12. Similarly, the detector 22 is controlled by a detector acquisition system 34. The data acquisition system 34 controls acquisition of the signals generated in the detector 22, such as by controlling the configuration and operation of the detector readout circuitry. In one embodiment, the data acquisition system 34 converts analog signals acquired from the readout electronics into digital signals. In other embodiments, the signals are digitized at the detector 22 and are provided to the data acquisition system 34 in a digital format. The data acquisition system 34 may also execute various calibration, signal processing, and filtration functions, such as for initial adjustment of dynamic ranges, interleaving of digital image data, and so forth, to condition the acquired signals for subsequent image processing. Similarly, the data acquisition system 34 may condition the data to represent the line integrals of the attenuation coefficients of the scanned object. The processed data, commonly called projections, may subsequently be filtered and backprojected to formulate an image of the scanned area. In the depicted embodiment, the X-ray controller 30 and data acquisition system 34 are part of a system controller 24 which commands operation of the imaging system 10 to execute examination protocols and to process acquired data.

As will be appreciated by those of ordinary skill in the art, the ends of the C-arm 14 rotate about an imaging volume. In some embodiments, the rotation may be accomplished manually, such as by the physical manipulation of an operator. In such embodiments, spatial and angular information about the position of the C-arm 14 may be collected during image acquisition, such as by one or more position sensors or motion detectors. Alternatively, in embodiments in which the motion of the C-arm 14 is automated or mechanized, a motor controller 34 may be incorporated into the system controller 24, as depicted in FIG. 1. In general the motor controller 34 controls the rotation of the C-arm 14 about the imaging volume, such as via a rotational subsystem. Furthermore, in embodiments, in which the C-arm 14 is linearly displaced relative to the patient 18 (either by motion of the C-arm 14 or by motion of the patient on an examination table) the motor controller 34 controls the linear displacement, such as by a linear positioning subsystem.

As will be appreciated by those of ordinary skill in the art, the depiction of the X-ray controller 30, data acquisition system 34, the motor controller 34, and the system controller 24 as discrete and discernible components is one of convenience to simplify the discussion of particular functions performed in imaging system 10. Indeed, in some exemplary embodiments the functionalities ascribed to the X-ray controller 30, the motor controller 34, and/or the data acquisition system 34 may be performed by dedicated circuits, as may be found in an application-specific computer, component, or controller. However, in other embodiments, the functionalities ascribed to the X-ray controller 30, the motor controller 34, and/or the data acquisition system 34 may be performed by general purpose circuitry, as may be found in a general purpose computer configured to execute suitable software routines for performing some or all of these functions. Therefore, some or all of the functionalities attributed to the system controller 24 for the purpose of discussion may be performed on dedicated circuits of a tangible controller, such as a system controller 24, or general purpose circuits of a general purpose computer configured to control an imaging system 10 in the manner described herein.

In the depicted embodiment of FIG. 1, the system controller 24, or a device providing some or all of the functionalities thereof, is coupled to a workstation 40, such as an image processing station, an image review station, and/or an operator console. As will be appreciated by one of ordinary skill in the art, the workstation 40 may be a general purpose or application-specific computer and may include the system controller 24 or circuitry (dedicated and/or general purpose) configured to perform the functions discussed above with regard to the system controller 24. Furthermore, the workstation 40 typically includes memory components (not shown), such as dynamic and/or static addressable memory media, which may be used to store acquired imaging data, imaging protocols and configurations, user specific configurations, patient information and medical history, and so forth. It should be understood that any type of computer accessible memory media capable of storing the desired amount of data and/or code may be utilized by such a workstation 40. Furthermore, the workstation 40 typically includes suitable network and device interfaces to allow communication between the workstation 40 and other devices, such as the scanning components of the imaging system 10, input devices (e.g., a mouse and/or keyboard), output devices (e.g., a display 42 and/or printer 44), and/or remote workstations 48, such as may be present on a common network.

As will be appreciated by those of ordinary skill in the art, generating high-quality three-dimensional images using an imaging system, such as the exemplary imaging system 10, requires accurate knowledge of the imaging geometry. To this end, the geometry of the imaging system 10 is typically calibrated prior to or during the acquisition of patient image data. The geometry of the imaging system 10 may be calibrated using a phantom or markers within the field of view of the system 10 or by using position sensors to measure the exact position and orientation of the source 12 and detector 22 at different orientations of the C-arm 14.

The exemplary system 10 of FIG. 1 may be used in the acquisition and reconstruction of two- and/or three-dimensional images in accordance with the present technique. However, as will be appreciated by those skilled in the art, reconstruction of two-dimensional and/or three-dimensional images may be complicated by a variety of factors. For example, images of dynamic tissue may include motion-related artifacts attributable to the movement of the tissue during acquisition of the image data. To reduce motion-related artifacts, it is generally desirable to improve the temporal resolution of the image reconstruction process. In the present technique, temporal resolution is improved by motion estimation as opposed to faster gantry rotation and data acquisition, which may be physically difficult to achieve.

Figure 2:
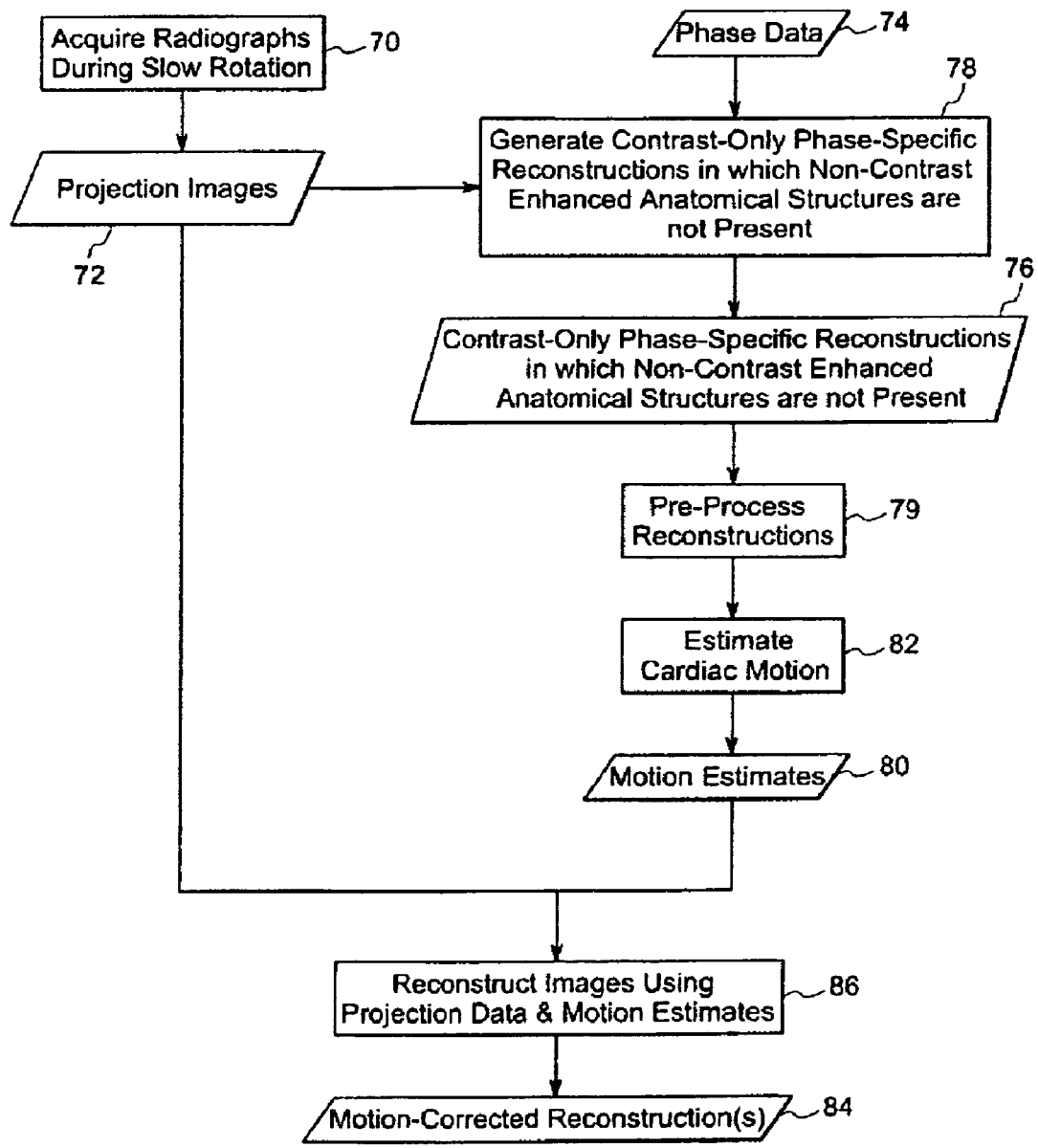
FIG. 2 is a flowchart depicting a technique for generating motion-corrected images of a moving object, in accordance with the present technique.

For example, referring to FIG. 2, a process for improving the effective temporal resolution of an image reconstruction process is depicted. As depicted at step 70, radiographs of the object within the field of view are acquired by one or more slowly rotating C-arms 14. In one embodiment, the image data is acquired by rotating the one or more C-arms 14 in a limited angular range of approximately 180° (typically 180° plus the fan angle of the X-ray beam 16) about the imaging volume. In this embodiment, each C-arm, and by extension, the associated source 12 and detector 22, as shown in FIG. 1, is rotated as slowly as possible subject to the constraint that the approximately 180° of rotation is completed within a breath hold of the patient, typically 20-30 seconds. During the rotation of each C-arm, acquisition of the image data by the source 12 and detector 22 proceeds at a high frame rate. In this embodiment, an image sequence is obtained over several heart cycles (typically between 15-30) with 30 or more images acquired per heart cycle. In further embodiments, the slow rotation may occur over the span of multiple breaths or without breath holding. In these embodiments, respiratory motion data may be used to correct for the effects of the respiratory motion. Respiratory motion data, which may be used to determine the existence of a breath hold in the first embodiment or to derive respiratory motion correction factors in the second embodiment, may be acquired using respiratory sensors or from the acquired image data. In embodiments in which image data is used, respiratory motion may be measured by tracking the motion of the diaphragm and/or ribs in the projection images, by monitoring the translation of the heart periphery, and/or by monitoring markers on the patient's body.

As will be appreciated by those of ordinary skill in the art, acquisition timing (such as detector readout timing and frequency) and/or acquisition geometry (such as the gantry trajectory) may be varied to improve aspects of image quality or to emphasize features of interest. For example, with regard to acquisition timing, the rate of image acquisition may be varied during the limited angular rotation. In such embodiments, image acquisition may proceed at a greater rate during those portions of the heart cycle associated with more rapid cardiac motion, as determined from an external source, such as an electrocardiogram, or from projections made based upon acquired image data. Similarly, the rotation speed of the C-arm 14 may be varied over the course of image acquisition in response to cardiac phase or other imaging protocol considerations.

In addition, in some embodiments, non-standard gantry trajectories may be employed. For example, a three-dimensional gantry trajectory may be employed which includes specific view angles particularly relevant for assessing cardiac function. Such a three-dimensional viewing trajectory may be further improved by including less clinically relevant view angle positions that contribute to data completeness for image reconstruction. Furthermore, as noted above with read to the exemplary imaging system 10, two or more C-arm gantries may be employed for image acquisition. In embodiments employing two or more C-arms 14, the number of projection images acquired at each phase of the cardiac cycle are increased for each heart cycle by the number of C-arm gantries employed. In addition, if orthogonal C-arms 14 are employed, orthogonal image pairs are concurrently acquired, which may be useful for image reconstruction and/or motion estimation.

The radiographs acquired during the slow rotation acquisition step 70 are processed to form a set of projection images 72. As will be appreciated by those of ordinary skill in the art, each projection image of the set 72 is acquired at some instant of the cardiac cycle such that each projection image may be characterized by what phase of the cardiac cycle it was acquired during, as well as its angular orientation. The number of phases of cardiac motion is arbitrary and generally depends on the degree of accuracy and temporal resolution to be achieved. For example, in one embodiment, the number of possible phases ranges from about 15 to about 50, with 30 phases being a typical selection. In one embodiment, each phase corresponds to an equal time interval. In another embodiment, however, the phases associated with periods of rapid cardiac motion are associated with shorter time intervals than those phases associated with little or slow cardiac motion. Furthermore, the number of projection images associated with each phase may or may not be equal. For example, in embodiments in which the phases do not correspond to equal time intervals and/or in which image acquisition is not temporally uniform, more projection images may be acquired for some phases than others. Based upon the number of desired phases, however, each projection image of the set 72 may be characterized as corresponding to a particular phase of cardiac motion.

In one embodiment, phase data 74 for the cardiac cycle is acquired or generated and used to differentially process the projection images 72 based upon each projection image's corresponding phase. In one embodiment, the phase data 74 is derived from the X-ray image data itself. In one example of such an embodiment, the phase data 74 is derived from projection images 72 themselves, such as via techniques employing consistency conditions to analyze the projection images 72 and/or to compare the moments of the projection data 72. In other embodiments, the phase data 74 is acquired from auxiliary sources, such as other imaging or cardiac monitoring modalities. For example, the phase data 74 may be derived from a concurrently acquired electrocardiogram (ECG) signal. Alternatively, the phase data 74 may be derived from non-X-ray imaging data acquired concurrently via other imaging modalities and/or sensing devices.

Based upon the projection images 72 and the phase data 74, phase-specific reconstructions 76 of the heart are generated at step 78. The phase-specific reconstructions 76 are typically three-dimensional representations of the heart reconstructed from the projection images 72 for each selected phase and, therefore, may be generated with projections from a limited number of views. In one embodiment, the reconstruction step 78 only utilizes the projection images 72 acquired during a given phase to reconstruct the phase-specific reconstruction 76 for that phase. In other embodiments, projection images 72 acquired in adjacent or proximate phases may also be used in the reconstruction of some or all of the phase-specific reconstructions 76. In such an embodiment, projection images 72 acquired at or near the phase of interest may be given greater weighting during the reconstruction step 78. Such a weighting may take the form of a confidence value associated with each projection image as a measure of how similar the projection image is relative to a projection image for the desired phase. In one embodiment, phases associated with diastole, during which little cardiac motion occurs, may be combined (or weighted highly or assigned a high confidence value) and used to generate a high-quality reference image. In this embodiment, the high-quality reference image may be useful in estimating the motion through the various phases associated with systole.

Any reconstruction technique that provides image quality suitable for motion estimation from the phase-specific reconstructions 76 may be employed at step 78. For example, a Feldkamp, Davis, and Kress (FDK) reconstruction algorithm may be employed in one embodiment. Similarly, a maximum likelihood transmission reconstruction (MLTR) approach (or suitable variations of such an approach) may be employed in another embodiment.

Furthermore, the reconstruction technique employed may incorporate one or more features to address data truncation issues arising from acquiring projection data from a limited portion of the detector 22 or from a detector not covering the full field of view, as discussed above. In other approaches, the FDK and/or MLTR algorithms used in reconstruction may be modified so that anatomy which is present in all of the projections is removed prior to reconstruction at step 78 (or at step 86 discussed below). Alternatively, the reconstruction algorithms may be modified to incorporate knowledge of the data incompleteness into the reconstruction process itself.

Data truncation issues may also be addressed by limiting reconstruction to contrast-only images. For example, an image acquisition sequence may be performed prior to the intravenous or intra-arterial injection of a contrast agent into the patient. The pre-contrast agent image data may be used as a three-dimensional anatomical mask that may be subtracted from the image data acquired in a subsequent image acquisition sequence to generate contrast only images. Due to the removal of the non-contrast enhanced anatomical structures, data truncation issues are largely circumvented.

In some embodiments, the limited view phase-specific reconstructions 76 may be pre-processed at step 79 to facilitate subsequent motion estimation processing. For example, the phase specific reconstructions 76 may be of low quality due to the limited number of projections 72 used in their formation, leading to streak artifacts or other aberrations within the reconstructed volumes. Furthermore, varying contrast concentrations over the course of acquisition at step 70 may lead to contrast variations in the reconstructions 78 that may be incorrectly perceived as motion. These visual aberrations as well as others may be addressed by pre-processing at step 79.

For example, in one embodiment, the pre-processing step 79, may be based on the assumption that the heart returns to the same position for a given phase in the heart cycle. Therefore, the voxel intensity is periodic with heart cycle. Ignoring the possibility of sudden transitions (or steps) in intensity, the variation in voxel intensity may be approximated by the combination of low frequency sinusoids. Such an approximation smoothes the voxel intensity variation. The pre-processing step 79 may, therefore, perform such approximations. The reconstruction data may then be smoothed, such as via a three-dimensional bi-lateral filter, as part of the pre-processing step 79. In such an embodiment, the three-dimensional bi-lateral filter may be selected or generated such that the sigma of the filter is sufficiently small as to minimize blurring of the blood pool-heart muscle boundary but large enough to smooth streak artifacts and blood pool contrast variations. Subsequent to filtration, the pre-processing step 79 may again approximate voxel intensity variations over the heart cycle by a combination of low frequency sinusoids to further smooth the reconstructions.

Other strategies may also be employed in the pre-processing step 79. For example, in another embodiment, a three-dimensional bi-lateral filter is applied recursively to the image data, reducing the image intensities to a small, discrete set. The voxel intensity variation over the heart cycle may then be approximated as a periodic set of steps. In a further embodiment, the pre-processing step 79 may recognize streaks in the image data and remove them directly. For example, a gradient may be calculated for each pixel in each slice of the volume using forward differences. In this embodiment, the image is then sampled at a point approximately one pixel along the gradient vector in the uphill and downhill directions. If the current pixel value is greater than both of these samples or less than both of the samples, the pixel is considered to be a streak. Neighborhood tests may be incorporated along the gradient to confirm the streak. The value of a pixel identified as part of a streak is replaced with a function of these sample points along the gradient vector (for example the mean of the uphill and downhill value). If the current pixel is in-between the intensities of the uphill and downhill values, then it is left unchanged. In this manner, one pixel wide streaks may be corrected during the pre-processing step 79. In yet another embodiment, the four-dimensional data is segmented on the basis of contours during the pre-processing step 79. The motion of contour boundaries may subsequently define the motion map. As will be appreciated by those of ordinary skill in the art, other nonlinear filtering operators may also be applied (such as anisotropic diffusion, curvature anisotropic diffusion, curvature flow, and so forth) in the pre-processing step 79 to condition the phase-specific reconstructions 76 for subsequent processing.

The limited-view phase-specific reconstructions 76, pre-processed or otherwise, are used to derive estimates 80 of cardiac motion (or deformation) at step 82. The step 82 of motion estimation may be based on a variety of techniques, some of which will be discussed herein, though other techniques are also possible and are usable in conjunction with the present technique. For example, such motion estimation techniques may include approaches that rely on non-rigid matching techniques, also known as deformable modeling. Such approaches take into account that the heart is not only moving, but also changing shape or deforming, during the cardiac cycle. Other types of modeling techniques may also be employed at step 82, some examples of which are discussed herein.

In some embodiments, motion estimation at step 82 may be feature based where features identified by one or more feature detecting routines (such as edge detection routines) calculate a motion field, such as with an iterative closest point technique. For example, in one embodiment, a feature detection routine is applied to an initial image. Detected features are mapped through the current estimate of the transformation (rigid body, affine, b-spline) used to align the initial image with a second image. The transformed or mapped features are used as the starting point for a spatial search to locate an image structure in the second image similar to the original detected features from the initial image. Such a spatial search may be bounded or otherwise constrained based on the desired computational resources to be applied or on known or presumed motion limitations for features within the imaged volume. Similarly, the spatial search may be directional, such as where information is known which would suggest that motion in certain directions is more likely than motion in other directions. The feature points for which correspondences can be determined are used to update the transformation that aligns the images under some metric, such as least squares.

In one embodiment, motion estimation at step 82 may be based upon locally adaptive thresholds. Such an embodiment allows variations in intensity over the imaged heart volume to be taken into account. In this embodiment the temporal image difference at a given slice location within the heart is normalized by local intensity range. Motion detection is then performed on the normalized difference.

In another embodiment, motion estimation at step 82 may be based on partial differential equation (PDE) or optical flow approaches. For example, a Demons algorithm is an example of non-rigid matching technique between source and target volumes, i.e, a deformable modeling technique, as mentioned above, which may be used in such a PDE-based approach. In this approach, it may be assumed that a cardiac volume may be described as a set of iso-contours. The normalized gradient of the target volume may then be used to describe the orientation of each voxel relative to the nearest iso-contour boundary. Differences between source and target images indicate where iso-contours do not match. The sign of the difference and the orientation of the normalized gradient specify the direction to move each voxel in the source to better match the target, whereas the magnitude of the difference dictates the magnitude of the movement.

This process can be represented as an iterative algorithm solving a partial differential equation in which the pushing force for each voxel is computed according to:

$$\vec{p} = \frac{(S-T)\vec{\nabla} T}{\vec{\nabla} T^2 + (S-T)^2} \quad (1)$$

where S is the source image, T is the target image, $\vec{p}$ is the pushing force, and $\vec{\nabla}$ is the gradient. The source image, S, may then be deformed according to $\vec{p}$. Alternatively, smoothing or regularization routines, such as application of a low pass filter, anisotropic or robust smoothing, or tensor based smoothing, may be applied to the pushing force $\vec{p}$ to generate $\vec{p}\,'$ after every iteration in the solution of the partial differential equation. As an alternative, the smoothing may be applied to just the change in the pushing force after every iteration in the solution of the partial differential equation or applied to both the pushing force and the change in the pushing force. In embodiments where smoothing is applied to the pushing force after every iteration, the solution may be regularized under an elastic constraint. Similarly, in embodiments where smoothing is applied to the change in the pushing force after every iteration, the solution may be regularized under a viscous constraint. In embodiments where smoothing is applied to both the pushing force and the change in the pushing force, the solution may be regularized under both elastic and viscous constraints. Regardless of how the pushing force is regularized, a new pushing force field $\vec{p}\,'$ is generated and the source image, S, may be deformed according to $\vec{p}\,'$. As will be appreciated by those of ordinary skill in the art, the term $(S-T)^2$ in the denominator of equation (1) is an ad hoc attempt to regularize $\vec{p}$. However, this attempt may be insufficient for cardiac volumes where, for example, voxels in the blood pool can have both $\vec{\nabla} T$ and $(S-T)$ approach 0 simultaneously causing $\vec{p}$ to become unstable. This problem may be mitigated by limiting the minimum value of $\vec{\nabla} T^2$ or in other ways familiar to those of skill in the art. Several termination criteria for a Demons algorithm may be employed, including limiting the number of iterations or employing a similarity threshold of the deformed source with the target image.

An example of a non-rigid matching technique which may be employed for motion estimation at step 82 is a four-dimensional motion estimation approach. Such an approach takes account of the fluidity and periodicity of cardiac motion in the motion estimation process. For example, one such non-rigid motion estimation that may be performed at step 82 includes performing a pair-wise volume non-rigid motion estimation. In this embodiment, a spline approximation of the motion trajectory over the heart cycle is then obtained. Using the spline approximation as an initial estimate, pair-wise volume motion estimation is then performed. The steps of obtaining the spline approximation and performing the pair-wise volume estimation based on the spline approximation may be iterated until a fixed number of iterations are performed or a convergence measure has been met.

In another embodiment, the motion estimation performed at step 82 is correlation based. In this approach, one or more regions of interest in the phase-specific reconstructions are correlated to respective regions in temporally proximate phase-specific reconstructions. Based on this correlation, the probable motion of the regions of interest over time may be determined and a displacement map generated based on the probabilistic motion data. In this manner, a displacement map may be generated for each projection image over time. The displacement and time information is combined to form a velocity map for each adjacent pair of phase-specific reconstructions 76 in one implementation. Once velocity and/or displacement maps are generated for each phase, the motion information may be further processed or used directly to warp the reconstruction grids during image reconstruction for the respective view angles.

In a similar embodiment, wavelet decomposition may be used in the motion determination step 82. In this approach one or more regions of interest in the phase-specific reconstructions 76 are decomposed via a wavelet function to generate wavelet coefficients for the regions of interest at each phase. One advantage of this approach is that the local frequency information of the regions of interest is better captured relative to approaches using Fourier-based analysis performed on the entire image. The differences between the wavelet coefficients associated with the regions of interest may be analyzed for regions in temporally proximate reconstructions to generate an image displacement map and/or velocity map describing the local motion of the regions of interest. Once the velocity and/or displacement maps of each phase are generated, the motion information incorporated in the maps may be used to warp the reconstruction grids for the respective view angles during image reconstruction.

In addition, the motion determination step 82 may include a multi-resolution aspect to augment the motion estimation technique employed. The multi-resolution aspect may be useful where the regions of interest exhibit complex or multiple directions of motion. In embodiments employing multi-resolution processing, the motion of the regions of interest, as identified in the velocity and/or displacement maps, is determined. An assessment is made as to whether temporally adjacent regions of interest are correlated to the desired degree, i.e., if a desired correlation threshold is met. For example, a correlation threshold of 95% may be implemented. If the correlation threshold is met, motion estimation proceeds in accordance with the implemented motion estimation technique, such as those described herein, with any remaining phases being processed and the motion information used to warp the respective reconstruction grids during image reconstruction. If, however, the correlation threshold is not met, the region or regions of interest may be subdivided and the correlation process repeated until the correlation threshold is met by the subdivided regions of interest. In this manner the complex motion of the heart, or other object, may be determined and accurately used to warp the reconstruction grids for subsequent image reconstruction.

In a further embodiment, the motion determination step 82 is accomplished using a sparse, differential-projection image grid motion determination approach. In this approach, the projection images 72 and the phase data 74 are used to reconstruct a reference image that is time-resolved image at a phase of minimum motion. The view angles of phases temporally proximate to the phase of minimum motion are identified using the phase data 74. The reference image is then forward-projected for the identified view angles and phase-specific displacement data is generated by optimizing, generally by minimizing, the difference between the forward-projected data and the measured projection data at the temporally proximate phases.

For example, in one implementation, minimizing the difference may be accomplished by generating a motion estimation map that appropriately warps the reconstruction grid during the increment in phase, thereby improving the similarity of the measured data with the forward-projected data. The motion estimates are considered accurate when little or no difference exists between the measured projection data of a phase and the corresponding forward-projected data after application of the phase-specific displacement data to the reconstruction grid.

As will be appreciated by those of ordinary skill in the art, optimization and/or minimization of the measured and projected differences may be accomplished by a variety of approaches. For example, the image motion may be linearized and solved iteratively. Alternatively, the problem may be expressed in terms of the optic flow equation, allowing the solution to be determined by the solution of a large set of linear equations. The process may also be accomplished by subtracting the forward-projected data from the measured projection data identified in a temporally proximate phase. The differential projection data thereby obtained may be backprojected to generate an image of the temporal derivative of the object motion in the image. The temporal derivative data may then be used to generate a gradient of the initial reference image while applying the constraint conditions for optic flow to estimate object motion occurring between reconstructed images of adjacent phases of interest.

The phase-specific displacement data thereby obtained provides a three-dimensional estimate of motion for the reference image. An image at the next temporal phase may then be generated by incorporating the image grid warping of the reconstructed images during the backprojection process. The process may be repeated until all phases of interest have been reconstructed. The phase-specific displacement data thereby generated may be used to warp the reconstruction grids at the respective view angles for subsequent image reconstruction processes.

This motion estimation approach may be modified by parameterizing the motion in the image using a three-dimensional function or set of three-dimensional basis functions. As one skilled in the art will readily understand, the same techniques can be applied to two-dimensional images as well. The coefficients of the functions or functions may be estimated from the displacement data to form a reconstructed image of the next phase. This approach provides a way to reconstruct a quantity based upon motion distribution as opposed to the linear attenuation coefficients visualized as intensities. Alternately, both the motion distribution and the linear attenuation can be reconstructed simultaneously in a similar fashion.

In another embodiment, motion estimation at step 82 may be accomplished by a time-resolved, differential-projection modeled motion determination approach. In this approach, the projection images 72 and the phase data 74 are used to identify a view angle associated with a phase of interest. The projection image acquired at the next adjacent view is subtracted from the projection image at the identified view to generate a differential signal representing the motion of the object between the two views along a substantially common ray. The motion of the heart may be estimated from the differential signal in accordance with the null space, i.e., the motion of the heart can be estimated orthogonal to, but not along the ray comprising the differential signal. If desired a correction factor may be introduced to account for the rotation of the heart, as represented in the differential signal.

If additional views of the phase of interest remain the process proceeds to the next view until all views of the phase of interest have been processed. The motion of the heart within the image may be determined from the combined differential signals. The respective reconstruction grids may be warped during image reconstruction at the respective view angles using the motion data determined from the combined differential signals. As will be appreciated by those of ordinary skill in the art, each phase of interest may be processed in this manner to until motion estimates are generated for each view of each phases of interest.

As will be appreciated by those of ordinary skill in the art, the preceding discussion of motion estimation techniques is not exhaustive, but is instead merely illustrative of the types of techniques that may be employed in the motion estimation step 82. Other motion estimation techniques may also be employed at motion estimation step 82 without departing from the scope of the present invention. Furthermore, to increase the probability that the motion estimates 80 closely match the actual cardiac motion, the estimation step 82 may also incorporate other sources of cardiac motion data, such as may be derived from other sensing or imaging modalities, to regularize the estimated motion field.

The motion estimates 80 are used to generate motion-corrected reconstructions 84, as depicted at step 86. Based upon the motion estimates 80, the reconstruction grid at each view angle associated with the projection images 72 may be warped or adapted to account for the motion of the heart. The projection images 72 are then reconstructed using the respective warped reconstruction grid for each view angle position to generate the motion-corrected reconstructions 84. In one embodiment, the degree of confidence in some or all of the motion estimates 80 may be factored into the reconstruction step 86. Such confidence values may vary for different cardiac phases and/or may vary for different spatial regions within the imaging volume. In embodiments in which confidence in the motion estimates is factored in to the reconstruction process, a maximum likelihood reconstruction technique may be employed. Other suitable reconstruction algorithms may also be employed.

In addition, in some embodiments, the generation of the motion-corrected reconstructions 84 at step 86 may include interpolation of estimated motion fields so that respective motion estimates 80 better represent the actual phase of corresponding projections. For example, where an acquired projection is generally intermediate between two phases, the motion associated with this projection may be better represented by an intermediate or interpolated value of the motion estimates for the two phases. In this manner, the motion for each projection may be estimated or interpolated to improve the quality of the motion-corrected reconstructions 84. As will be appreciated by those of ordinary skill in the art, embodiments employing such interpolation of the motion field may be more desirable when fewer phases are defined as the likelihood of projections being intermediate between phases increases as the number of phases decreases (i.e., as each phase corresponds to a greater time interval). Conversely, in embodiments where large numbers of phases are defined, each phase generally corresponds to a smaller time interval and the desirability of interpolating the motion field of some or all of the projections may be less.

Once the desired motion-corrected reconstructions 84 have been generated, the reconstructions may be associated spatially and/or temporally. For example, spatially proximate or adjacent images may be ordered or combined to generate a static volume rendering at one instant in the cardiac cycle or at a desired phase. Similarly, temporally proximate or adjacent images may be sequentially combined to generate an image sequence or video depicting a slice or cross-section over time, i.e., over the course of the cardiac cycle. Similarly, the motion-corrected reconstructions 84 may be associated both spatially and temporally to generate a dynamic volume rendering depicting the motion of the volume over time.

As will be appreciated by those of ordinary skill in the art, the present technique has many applications in cardiac assessment and/or for interventional procedures. For example, the present technique may be useful in quantifying ventricular and atrial function in three-dimensions throughout the cardiac cycle. In particular, cardiac diagnostic functions may be enhanced to the extent that local measurements, such as heart wall function, may be made to assess abnormalities and plan appropriate intervention. In particular, the present technique provides a non-invasive procedure to view coronaries which would allow coronary artery disease to be detected and assessed.

Additionally, the present technique may be useful in assessing a patient's electro-physiology, thereby allowing mapping of the acquired electrical information to an accurate three-dimensional representation of the heart cycle over time. In this manner, a three-dimensional, anatomical and functional view of the cardiac cycle over time may be generated. For example, in one implementation, the dynamic three-dimensional views attainable by the present technique may be visually modified (such as by color coding, shading, or other visual indications) to reflect electrical information. In this manner, cardiac wall and/or valve function may be assessed and, in particular, the coordination of the cardiac wall and valve functions may be viewed. Among other uses, such assessments and views may be useful for diagnostic purposes or in the preparation for and/or execution of interventional procedures.

Similarly, the three-dimensional motion-corrected reconstructions 84 generated in accordance with the present technique may be used for 2D/3D image fusion, such as where real-time two-dimensional fluoroscopy data is presented in the context of a previously acquired three-dimensional volume, here the motion-corrected reconstructions 84. Such a technique may further benefit from the presence of temporal information in the motion-corrected reconstructions 84, i.e., the full motion of the cardiac cycle may be represented if desired. Such applications may be of particular interest in catheterization procedures or other interventional techniques.

While the above techniques are useful in the determination of cardiac motion for use in reconstructing motion-corrected images and for improving the temporal resolution of reconstructed images, other techniques may also be employed and are within the scope of this disclosure. Likewise, the present techniques for reconstructing motion-corrected images and for determining motion may be applied to the imaging of moving objects other than the heart, including imaging of inanimate objects. Indeed, discussion of cardiac imaging is presented merely to facilitate explanation of the present techniques. Additionally, use of the motion estimates in the invention has been discussed in the context of FDK and MLTR reconstruction techniques. However, the motion estimates may be used with other reconstruction strategies, such as with iterative reconstruction techniques.

Furthermore, though the present techniques are discussed in the context of vascular imaging using an X-ray vascular C-arm system, other applications and modalities may benefit from the use of the present motion estimation and/or motion compensated reconstruction techniques. For example, tagged magnetic resonance (MR) techniques, such as may be used in cardiac imaging, may also benefit from the present techniques for motion estimation and/or motion compensated reconstruction. Similarly, imaging techniques with long acquisition times, such as nuclear imaging, positron emission tomography (PET), or single-photon emission computed tomography (SPECT), may benefit from the present motion estimation and/or motion compensated reconstruction techniques. For example, the present techniques may be useful in compensating for patient motion, such as respiratory motion, during the lengthy image data acquisition process. Indeed, the present techniques for motion estimation and/or motion compensated reconstruction techniques are believed to be generally useful for a variety of imaging techniques used to generate images of organs or objects undergoing periodic motion, even where such motion is not of constant frequency.

As one of ordinary skill in the art will appreciate, the processes for estimating motion and/or for reconstruction of phase-specific and/or motion-corrected images described herein may be provided as one or more routines executable by the workstation 40 or by other processor-based components of the imaging system 10 (FIG. 1). The routines may be stored or accessed on one or more computer-readable media, such as magnetic or optical media, which may be local to the workstation 40 or processor-based component or may be remotely accessible via a network connection, such as via the Internet or a local area network. Furthermore, access to or operation of the routines may be provided to an operator as part of the normal operation of an imaging system 10.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for generating phase-specific reconstructions, comprising:
    acquiring a plurality of projection images by moving an X-ray source about an imaging volume such that the X-ray source moves approximately 180 degrees;
    generating a plurality of phase-specific reconstructions in which anatomical structures imaged by a detector covering less than a full field of view are not present, wherein each phase-specific reconstruction is generated based on at least a subset of the plurality of projections acquired at or near the respective phase;
    generating a plurality of motion estimates based upon the plurality of phase-specific reconstructions; and
    generating one or more motion-corrected reconstructions, wherein each motion-corrected reconstruction is generated based on at least one respective motion estimate and on a corresponding subset of the plurality of projections.

2. The method as recited in claim 1, wherein acquiring the plurality of projection images comprises moving a C-arm.

3. The method as recited in claim 1, wherein acquiring the plurality of projection images comprises reading out a limited portion of a detector panel.

4. The method as recited in claim 1, wherein acquiring the plurality of projection images comprises varying an image acquisition rate.

5. The method as recited in claim 1, wherein acquiring the plurality of projection images comprises varying the speed at which the X-ray source moves.

6. The method as recited in claim 1, wherein the subset of the plurality of projections comprises only projections acquired during the respective phase.

7. The method as recited in claim 1, wherein the subset of the plurality of projections comprises a set of projections acquired during the respective phase and during proximate phases.

8. The method as recited in claim 1, comprising:
    associating two or more motion-corrected reconstructions spatially and/or temporally.

9. A computer-readable media, comprising:
    a routine for acquiring a plurality of projection images by moving an X-ray source about an imaging volume such that the X-ray source moves approximately 180 degrees;
    a routine for generating a plurality of phase-specific reconstructions in which anatomical structures imaged by a detector covering less than a full field of view are not present, wherein each phase-specific reconstruction is generated based on at least a subset of the plurality of projections acquired at or near the respective phase;
    a routine for generating a plurality of motion estimates based upon the plurality of phase-specific reconstructions; and
    a routine for generating one or more motion-corrected reconstructions, wherein each motion-corrected reconstruction is generated based on at least one respective motion estimate and on a corresponding subset of the plurality of projections.

10. The computer-readable media as recited in claim 9, comprising:
    a routine for associating two or more motion-corrected reconstructions spatially and/or temporally.

11. An image analysis system, comprising:
    a workstation configured to:
        generate a plurality of phase-specific reconstructions in which anatomical structures imaged by a detector covering less than a full field of view are not present, wherein each phase-specific reconstruction is generated based on at least a subset of projections acquired at or near the respective phase, and wherein the subset is part of a plurality of projections acquired by moving an X-ray source about an imaging volume such that the X-ray source moves approximately 180 degrees;
        generate a plurality of motion estimates based upon the plurality of phase-specific reconstructions; and
        generate one or more motion-corrected reconstructions, wherein each motion-corrected reconstruction is generated based on at least one respective motion estimate and on a corresponding subset of the plurality of projections.

12. The image analysis system as recited in claim 11, wherein the workstation is configured to associate two or more motion-corrected reconstructions spatially and/or temporally.

13. The image analysis system as recited in claim 11, comprising:
    a C-arm gantry comprising the X-ray source and a detector array;
    an X-ray controller configured to operate the X-ray source; and
    a data acquisition system configured to acquire a plurality of signals from the detector array, wherein the plurality of signals are processed by one of the data acquisition system or the workstation to generate the plurality of projections.

* * * * *

UNITED STATES PATENT AND TRADEMARK OFFICE
CERTIFICATE OF CORRECTION

PATENT NO. : 7,782,998 B2 Page 1 of 1
APPLICATION NO. : 11/018030
DATED : August 24, 2010
INVENTOR(S) : Langan et al.

It is certified that error appears in the above-identified patent and that said Letters Patent is hereby corrected as shown below:

In Column 4, Lines 44-45, delete "controller 34" and insert -- controller 32 --, therefor.

In Column 4, Line 46, delete "controller 34" and insert -- controller 32 --, therefor.

In Column 4, Line 52, delete "controller 34" and insert -- controller 32 --, therefor.

In Column 4, Line 56, delete "controller 34," and insert -- controller 32, --, therefor.

In Column 4, Line 61, delete "controller 34," and insert -- controller 32, --, therefor.

In Column 4, Lines 65-66, delete "controller 34," and insert -- controller 32, --, therefor.

Signed and Sealed this

Nineteenth Day of October, 2010

David J. Kappos
*Director of the United States Patent and Trademark Office*